(12) United States Patent
Nakajima

(10) Patent No.: US 10,609,297 B2
(45) Date of Patent: Mar. 31, 2020

(54) OPTICAL SCANNING ENDOSCOPE APPARATUS WITH LIGHT AMOUNT DETECTOR

(71) Applicant: OLYMPUS CORPORATION, Tokyo (JP)

(72) Inventor: Keiichiro Nakajima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 406 days.

(21) Appl. No.: 15/382,848

(22) Filed: Dec. 19, 2016

(65) Prior Publication Data
US 2017/0099421 A1    Apr. 6, 2017

Related U.S. Application Data

(63) Continuation of application No. PCT/JP2015/003083, filed on Jun. 19, 2015.

(30) Foreign Application Priority Data

Jun. 19, 2014    (JP) ................................ 2014-126163

(51) Int. Cl.
A61B 1/06    (2006.01)
A61B 1/07    (2006.01)
(Continued)

(52) U.S. Cl.
CPC ....... H04N 5/2354 (2013.01); A61B 1/00006 (2013.01); A61B 1/00165 (2013.01);
(Continued)

(58) Field of Classification Search
CPC ............ A61B 1/00006; A61B 1/00165; A61B 1/00186; A61B 1/0661; A61B 1/07;
(Continued)

(56) References Cited

U.S. PATENT DOCUMENTS 4,602,281 A    7/1986   Nagasaki et al.
5,475,420 A  * 12/1995   Buchin ................ A61B 1/0005
                                                              348/65
(Continued)

FOREIGN PATENT DOCUMENTS

CN         1561639 A       1/2005
CN       102781306 A      11/2012
(Continued)

OTHER PUBLICATIONS

Chinese Office Action dated Feb. 12, 2018 in Chinese Patent Application No. 201580032086.9.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

The disclosed optical scanning endoscope apparatus includes a scanner that scans an object with illumination light from a light source, a light amount detector that detects a light amount of the illumination light from the light source, and a controller that controls output of the light source based on the light amount detected by the light amount detector. The controller controls the output of the light source based on an integral value of the light amount detected by the light amount detector during an immediately prior predetermined period.

15 Claims, 9 Drawing Sheets

(51) Int. Cl.
   *H04N 5/235* (2006.01)
   *G02B 23/26* (2006.01)
   *H04N 3/02* (2006.01)
   *A61B 1/00* (2006.01)
   *G02B 23/24* (2006.01)
   *H04N 5/225* (2006.01)
   *H04N 5/378* (2011.01)

(52) U.S. Cl.
   CPC ........ *A61B 1/00186* (2013.01); *A61B 1/0661* (2013.01); *A61B 1/07* (2013.01); *G02B 23/2461* (2013.01); *G02B 23/26* (2013.01); *H04N 3/02* (2013.01); *H04N 5/2256* (2013.01); *H04N 5/378* (2013.01); *A61B 1/00172* (2013.01); *H04N 2005/2255* (2013.01)

(58) Field of Classification Search
   CPC ...... G02B 23/2461; G02B 23/26; H04N 3/02; H04N 3/2256; H04N 3/378; H04N 3/2354
   See application file for complete search history.

(56) References Cited

U.S. PATENT DOCUMENTS

| | | | | |
|---|---|---|---|---|
| 5,730,702 A | * | 3/1998 | Tanaka | A61B 1/05 362/276 |
| 6,320,331 B1 | * | 11/2001 | Iida | H05B 37/03 315/129 |
| 2002/0093563 A1 | * | 7/2002 | Cline | A61B 1/00009 348/65 |
| 2007/0225560 A1 | * | 9/2007 | Avni | A61B 1/00006 600/118 |
| 2011/0158914 A1 | * | 6/2011 | Yamada | A61B 1/045 424/9.6 |
| 2012/0035419 A1 | * | 2/2012 | Ashida | A61B 1/00009 600/109 |
| 2012/0190922 A1 | * | 7/2012 | Kaku | A61B 1/00009 600/109 |
| 2014/0180012 A1 | * | 6/2014 | Yoshino | A61B 1/00006 600/180 |
| 2014/0284460 A1 | * | 9/2014 | Nishimura | A61B 1/00172 250/214.1 |

FOREIGN PATENT DOCUMENTS

| | | |
|---|---|---|
| JP | 60-55924 A | 4/1985 |
| JP | 2004-194821 A | 7/2004 |
| JP | 2006-247404 A | 9/2006 |
| JP | 2010-115391 A | 5/2010 |
| WO | 2014/041847 A1 | 3/2014 |

OTHER PUBLICATIONS

Chinese Office Action dated Aug. 3, 2017 in Chinese Patent Application No. 201580032086.9.

Japanese Office Action dated Nov. 7, 2017 in Japanese Patent Application No. 2014-126163.

ISR dated Sep. 1, 2015 from related PCT/JP2015/003083.

* cited by examiner

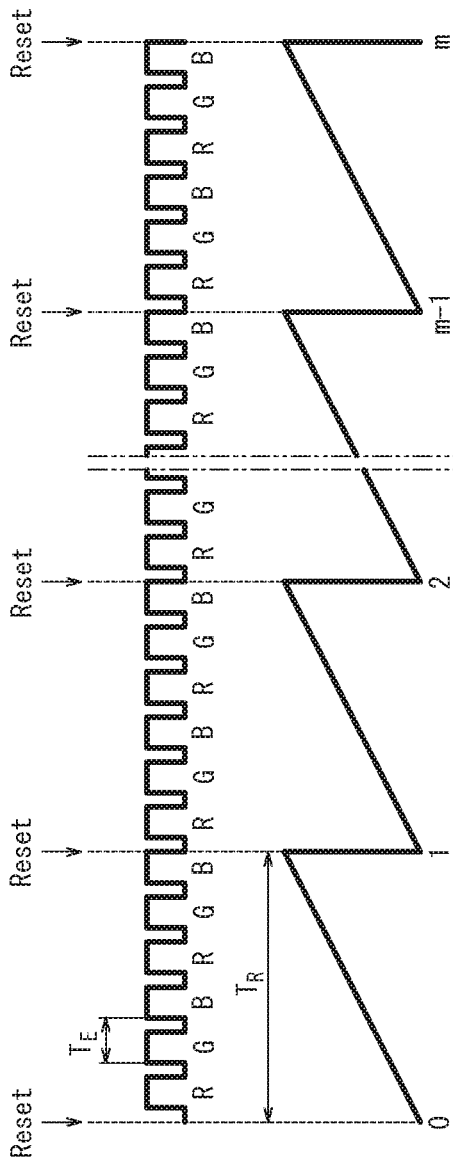
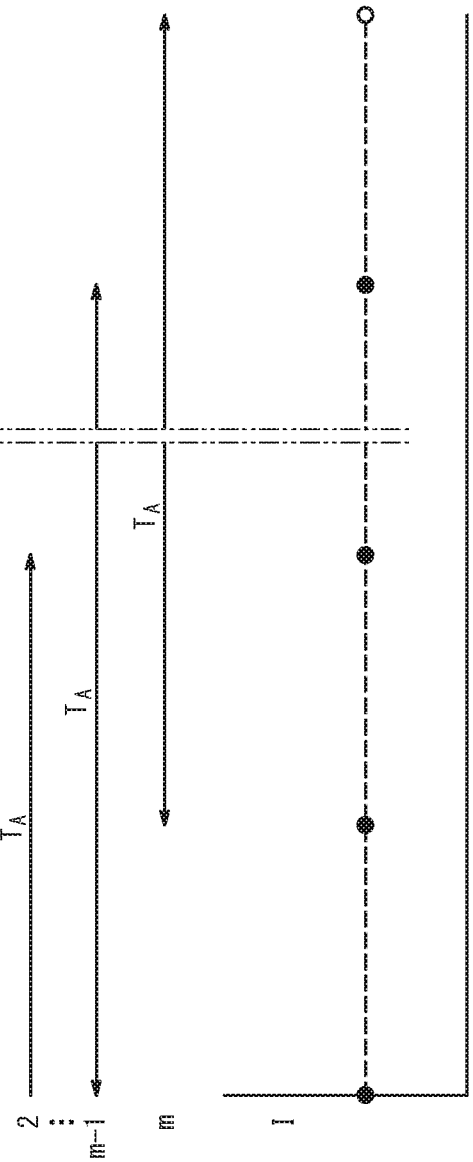
FIG. 6A Input light
FIG. 6B Integral output
FIG. 6C Integration period
FIG. 6D Integration result

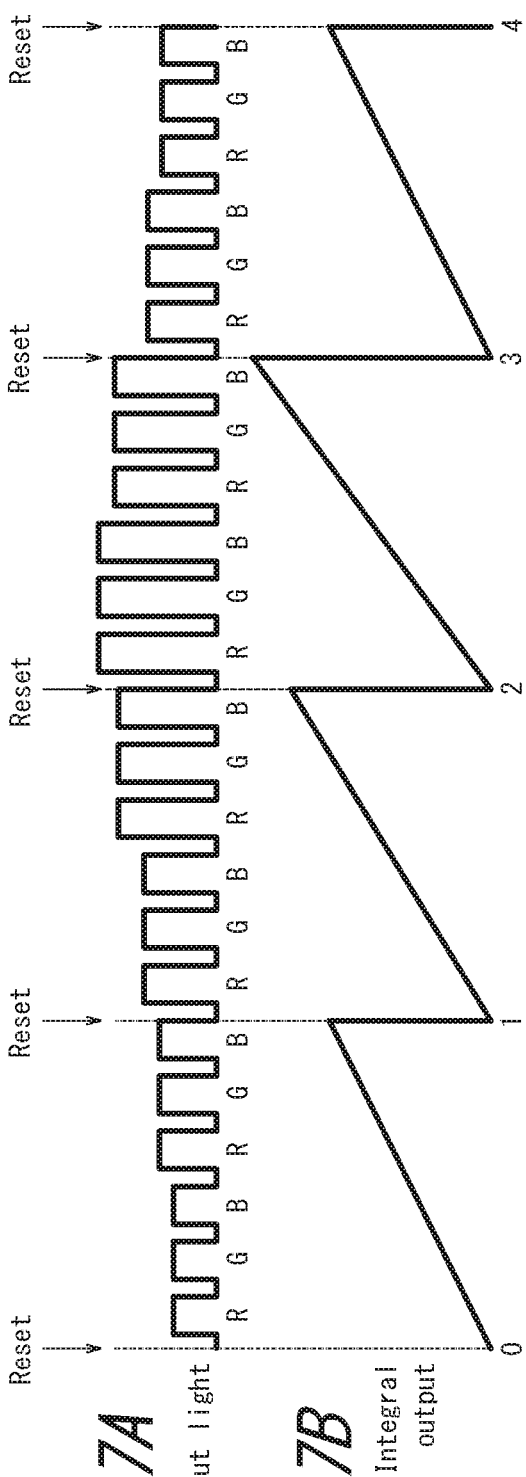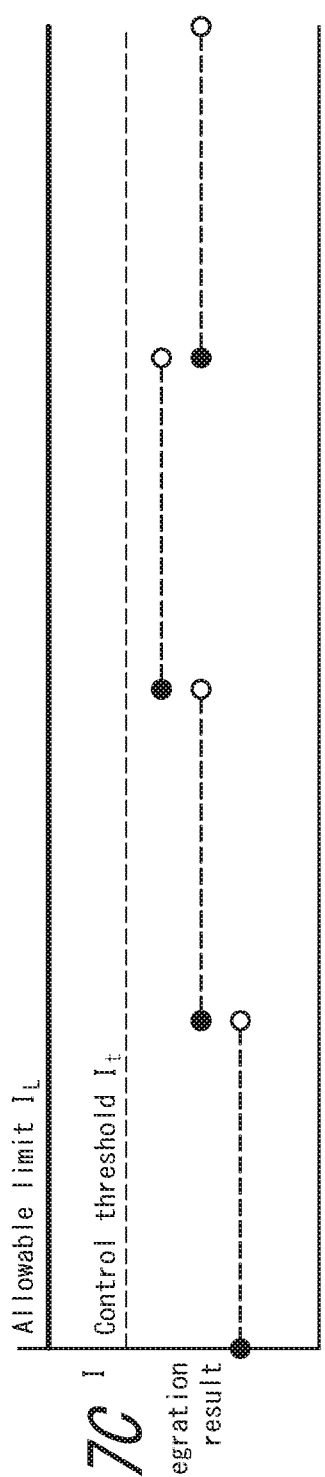

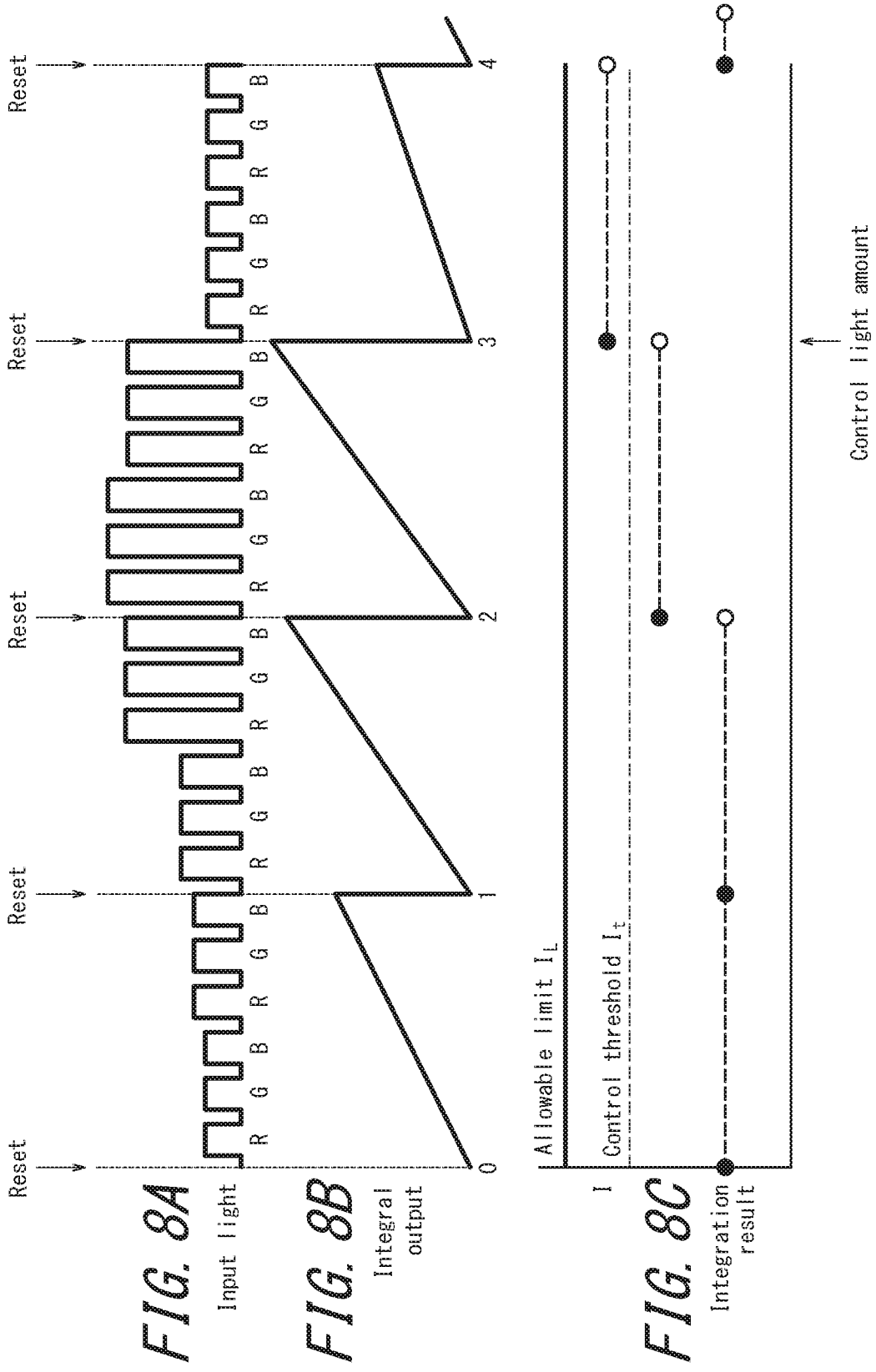

OPTICAL SCANNING ENDOSCOPE APPARATUS WITH LIGHT AMOUNT DETECTOR

CROSS-REFERENCE TO RELATED APPLICATION

The present application is a Continuing Application based on International Application PCT/JP2015/003083 filed on Jun. 19, 2015, which in turn claims priority to Japanese Patent Application No. 2014-126163 filed on Jun. 19, 2014, the entire disclosure of these earlier applications being incorporated herein by reference.

TECHNICAL FIELD

This disclosure relates to an optical scanning endoscope apparatus for optically scanning an object.

BACKGROUND

One known example of an optical scanning endoscope apparatus detects a luminance level based on reflected light from an object illuminated with light and controls the amount of illumination light in accordance with scanning position by setting the amount of illumination light so that, in the observation image, the light amount is reduced as the luminance level is brighter at the scanning position and is increased as the luminance level is darker at the scanning position (for example, see JP 2010-115391 A (PTL 1)).

CITATION LIST

Patent Literature

PTL 1: JP 2010-115391 A

SUMMARY

To this end, an optical scanning endoscope apparatus according to this disclosure includes:
a scanner configured to scan an object with illumination light from a light source;
a light amount detector configured to detect a light amount of the illumination light from the light source; and
a controller configured to control output of the light source based on the light amount detected by the light amount detector;
the controller controlling the output of the light source based on an integral value of the light amount detected by the light amount detector during an immediately prior predetermined period.

The controller preferably suspends the output of the light source based on the integral value of the light amount.

The controller preferably lowers the light amount of the illumination light from the light source based on the integral value of the light amount to a light amount lower than an average light amount of the illumination light from the light source during the immediately prior predetermined period.

When the integral value of the light amount exceeds a predetermined threshold, the controller preferably controls the output of the light source so that the integral value of the light amount does not exceed a predetermined allowable limit that is higher than the predetermined threshold.

The light amount detector preferably includes:
a monitor photodetector configured to detect the illumination light from the light source;
a corrector configured to correct a light detection signal from the monitor photodetector in accordance with wavelength of the illumination light; and
an integrator configured to calculate the light amount based on the light detection signal corrected by the corrector.

BRIEF DESCRIPTION OF THE DRAWINGS

In the accompanying drawings:
FIGS. 6A, 6B, 6C, and 6D illustrate operations by the light amount detector and the controller in FIG. 1;
FIGS. 7A, 7B, and 7C illustrate an example of operations by the controller;
FIGS. 8A, 8B, and 8C illustrate another example of operations by the controller;
FIG. 9A is a cross-sectional diagram of the tip of the scope,
FIG. 9B is an enlarged perspective view of the driver in FIG. 9A,
and FIG. 9C is a cross-sectional view along a plane perpendicular to the axis of the optical fiber, illustrating a portion including the coils for generation of a deflecting magnetic field and the permanent magnet in FIG. 9B.

DETAILED DESCRIPTION

Embodiments are described below with reference to the drawings.

Embodiment 1

Figure 1:
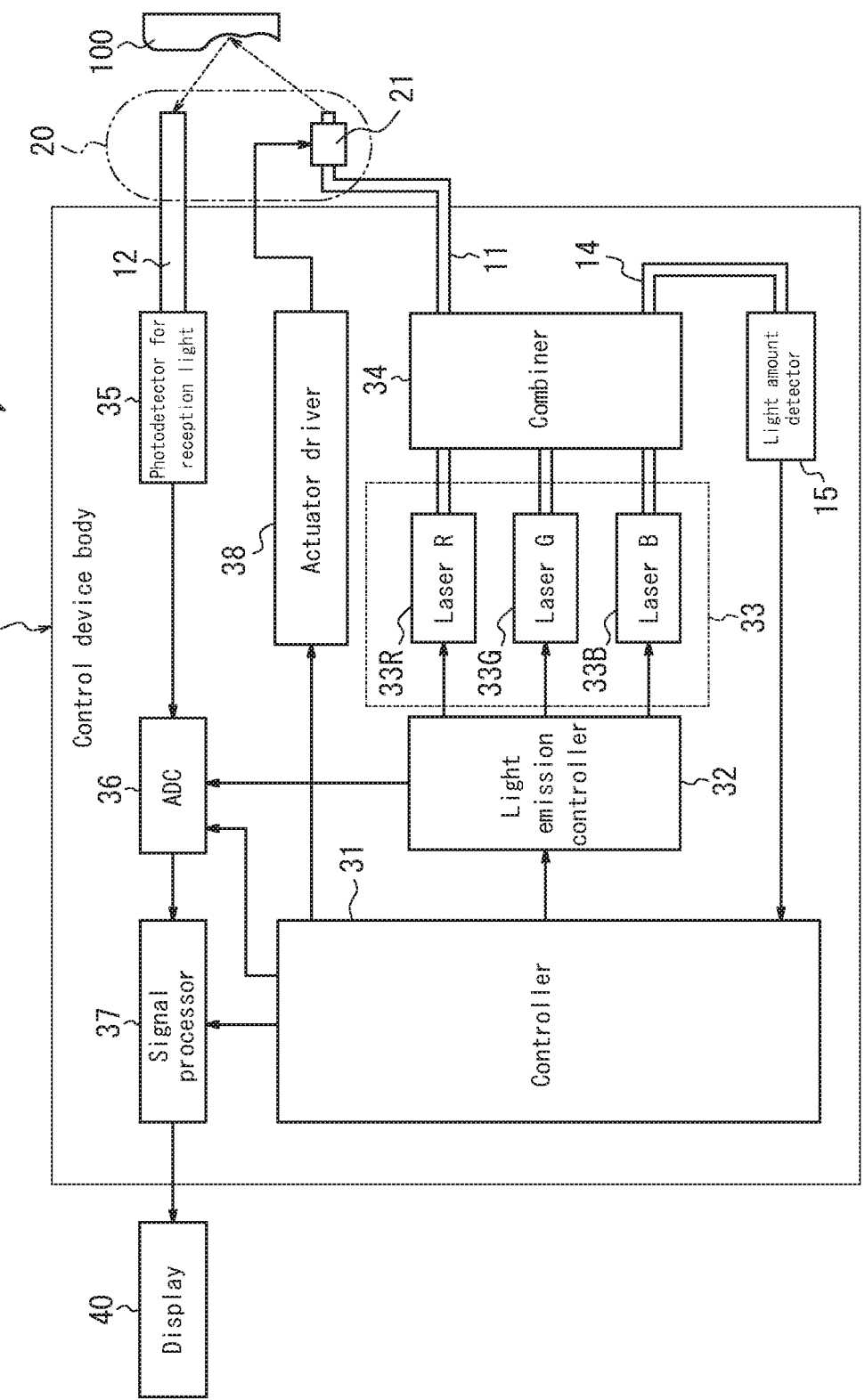
FIG. 1 is a block diagram schematically illustrating the structure of an optical scanning endoscope apparatus according to Embodiment 1.

With reference to FIGS. 1 to 8C, Embodiment 1 is described. FIG. 1 is a block diagram schematically illustrating the structure of an optical scanning endoscope apparatus according to Embodiment 1. In FIG. 1, an optical scanning endoscope apparatus 10 includes a scope 20, a control device body 30, and a display 40.

First, the structure of the control device body 30 is described. The control device body 30 includes a controller 31 that controls the optical scanning endoscope apparatus 10 overall, a light emission controller 32, lasers 33R, 33G, and 33B (the lasers 33R, 33G, and 33B also being collectively referred to below as a "light source 33"), a combiner 34, an actuator driver 38, a photodetector 35 for reception light, an analog/digital converter (ADC) 36, a signal processor 37, a monitor fiber 14, and a light amount detector 15.

In accordance with control by the light emission controller 32, the light source 33 constituted by the lasers 33R, 33G, and 33B selectively emits illumination light of a plurality of different wavelengths (in this embodiment, illumination light of three wavelengths: R, G, and B). As used herein, "selectively emits illumination light of a plurality of different wavelengths" refers to illumination light of one wavelength selected by the light emission controller 32 being emitted at a timing selected by the light emission controller 32. For example, Diode-Pumped Solid-State (DPSS) lasers or laser diodes may be used as the lasers 33R, 33G, and 33B.

In response to a control signal from the controller 31, the light emission controller 32 controls the light emission timing of the light source 33. In this embodiment, during one scan, the light emission controller 32 switches the wavelength of the R, G, or B illumination light from the light source 33 in a predetermined light emission order (in this example, in the order R, G, B) at constant time intervals (light emission cycle $T_E$).

As used here, "one scan" refers to one scan, in order to capture one image, from the starting point to the ending point of a predetermined scan path, such as a spiral. Furthermore, the "light emission cycle $T_E$" does not refer to the light emission cycle of each of the lasers 33R, 33G, and 33B constituting the light source 33, but rather to the light emission cycle of illumination light that is sequentially emitted from the light source 33.

The laser illumination light emitted from the lasers 33R, 33G, and 33B passes through optical paths joined coaxially by the combiner 34 and is incident as illumination light on a light transmission fiber 11, which is a single-mode fiber. The combiner 34 also partitions, to the light amount detector 15, a certain proportion of the output for the light transmission fiber 11. Since this proportion is nearly unaffected over time, a reduction in the accuracy of measurement, by the light amount detector 15, of the light amount is suppressed.

The combiner 34 may, for example, be configured using a fiber multiplexer, a dichroic prism, or the like.

The lasers 33R, 33G, and 33B and the combiner 34 may be stored in a housing that is separate from the control device body 30 and is joined to the control device body 30 by a signal wire.

Illumination light incident on the light transmission fiber 11 from the combiner 34 is guided to the tip of the scope 20 and irradiated onto an object 100. At this time, by driving the actuator 21 of the scope 20 by vibration, the actuator driver 38 of the control device body 30 drives the tip of the light transmission fiber 11 by vibration. As a result, the illumination light emitted from the light transmission fiber 11 scans the observation surface of the object 100 in 2D along a predetermined scan path. Reception light such as reflected light or scattered light that is obtained from the object 100 due to irradiation with the illumination light is received at the tip of a light-receiving fiber 12, which is constituted by multi-mode fibers, and is guided through the scope 20 to the control device body 30.

In this example, the light transmission fiber 11 and the actuator 21 constitute a scanner that scans illumination light from the light source 33 over the object 100.

The photodetector 35 for reception light detects reception light from the object 100 through the light-receiving fiber 12, the reception light being obtained by irradiation of illumination light at the wavelength (also referred to below as the color) of one of R, G, and B at each light emission cycle $T_E$ of the light source 33, and outputs an analog signal (electrical signal).

The ADC 36 converts the analog signal from the photodetector 35 for reception light to a digital signal (electrical signal) and outputs the result to the signal processor 37.

The signal processor 37 associates the digital signals, which correspond to the various wavelengths and were input from the ADC 36 at each light emission cycle $T_E$, with the respective light emission timings and scanning positions, and stores the results sequentially in memory (not illustrated). Information on the light emission timing and scanning position is acquired from the controller 31. The controller 31 calculates information on the scanning position along the scanning path from information such as the amplitude and phase of vibration voltage applied by the actuator driver 38. After completion of scanning or during scanning, the signal processor 37 generates an image signal by performing image processing as necessary, such as enhancement, γ processing, and interpolation, based on each digital signal input from the ADC 36 and displays an image of the object 100 on the display 40.

The monitor fiber 14 is an optical fiber connecting the combiner 34 with the light amount detector 15 and guides, to the light amount detector 15, a certain proportion of the output for the light transmission fiber 11 from the combiner 34.

The light amount detector 15 detects the light amount of illumination light from the light source 33 and notifies the controller 31 of the detected light amount. As described below, the controller 31 controls the output of the light source 33 based on the integral value I of the light amount detected by the light amount detector 15 during the immediately prior predetermined integration period $T_A$.

Further details on the light amount detector 15 are provided below.

Figure 2:
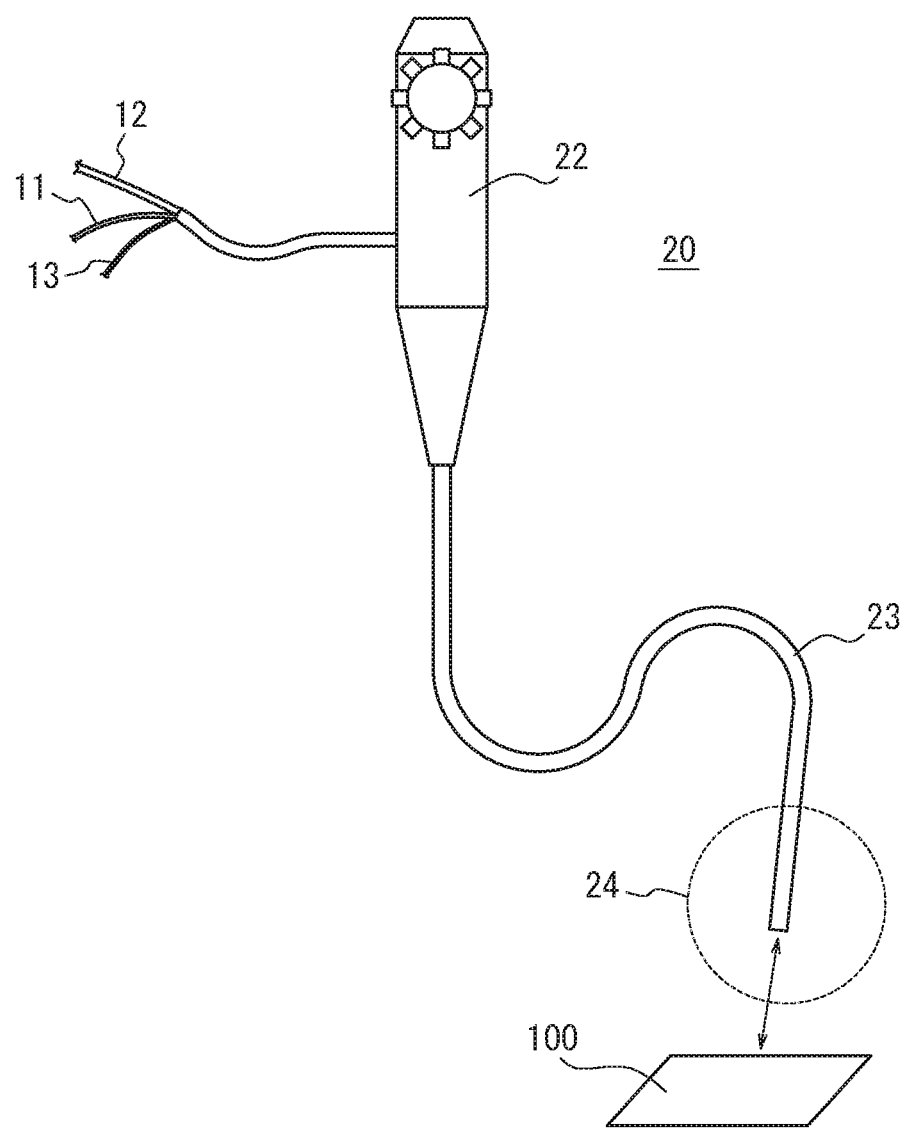
FIG. 2 is a schematic overview of the scope in FIG. 1.

Next, the structure of the scope 20 is described. FIG. 2 is a schematic overview of the scope 20. The scope 20 includes an operation part 22 and an insertion part 23. The light transmission fiber 11, the light-receiving fiber 12, and a wiring cable 13 that extend from the control device body 30 are each connected to the operation part 22. The light transmission fiber 11, light-receiving fiber 12, and wiring cable 13 pass through the insertion part 23 and extend to a tip 24 (the portion within the dotted line in FIG. 2) of the insertion part 23.

Figure 3:
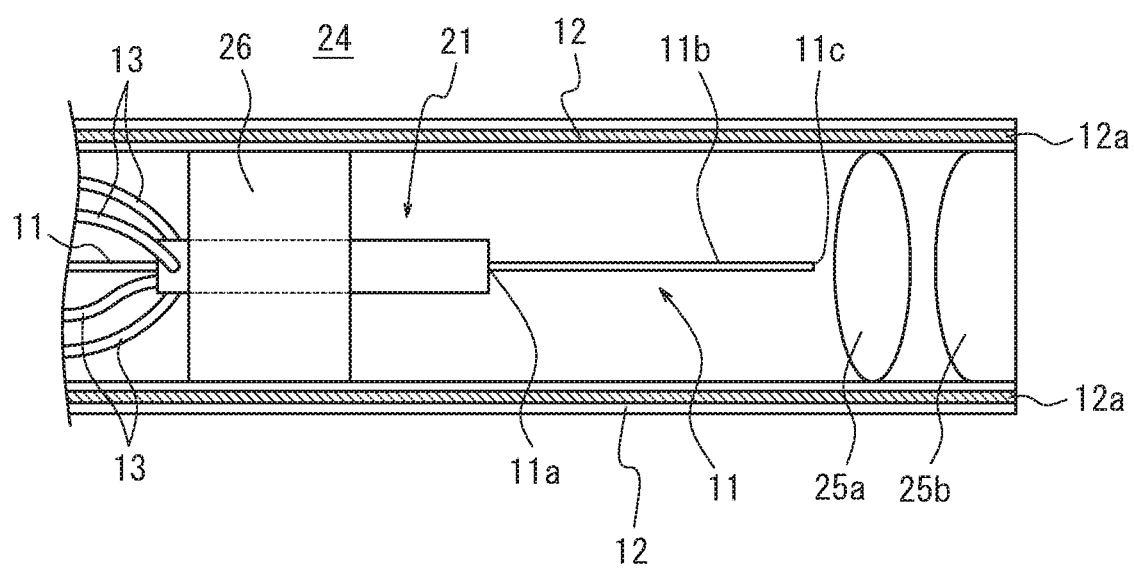
FIG. 3 is a cross-sectional diagram of the tip of the scope in FIG. 2.

FIG. 3 is a cross-sectional diagram illustrating an enlargement of the tip 24 of the insertion part 23 of the scope 20 in FIG. 2. The tip 24 of the insertion part 23 of the scope 20 includes the actuator 21, projection lenses 25a and 25b (optical system), the light transmission fiber 11 that passes through the central portion, and the light-receiving fiber 12 that passes through the peripheral portion and is constituted by an optical fiber bundle.

The actuator 21 drives a tip 11c of the light transmission fiber 11 by vibration. The actuator 21 includes a fiber holding member 29 fixed to the inside of the insertion part 23 of the scope 20 by an attachment ring 26 and piezoelectric elements 28a to 28d (see FIGS. 4A and 4B). The light transmission fiber 11 is supported by the fiber holding member 29, and the portion from a fixed end 11a supported by the fiber holding member 29 to the tip 11c is an oscillating part 11b that is supported to allow oscillation. The light-receiving fiber 12 is disposed to pass through the peripheral portion of the insertion part 23 and extends to the end of the tip 24. A non-illustrated detection lens is also provided at the tip of each fiber in the light-receiving fiber 12.

Furthermore, the projection lenses 25a and 25b and the detection lenses are disposed at the extreme end of the tip 24 of the insertion part 23 in the scope 20. The projection lenses 25a and 25b are configured so that laser illumination light emitted from the tip 11c of the light transmission fiber 11 is irradiated on the object 100 and roughly concentrated. The detection lenses are disposed so as to capture reception light that is reflected, scattered, or the like by the object 100 due to laser illumination light concentrated on the object 100 or florescent light generated by irradiation of laser illumination light concentrated on the object 100 (reception light obtained from the object 100), to concentrate the reception light on the light-receiving fiber 12 disposed behind the detection lenses, and to combine the reception light. The projection lenses are not limited to a double lens structure and may be structured as a single lens or as three or more lenses.

Figure 4A:
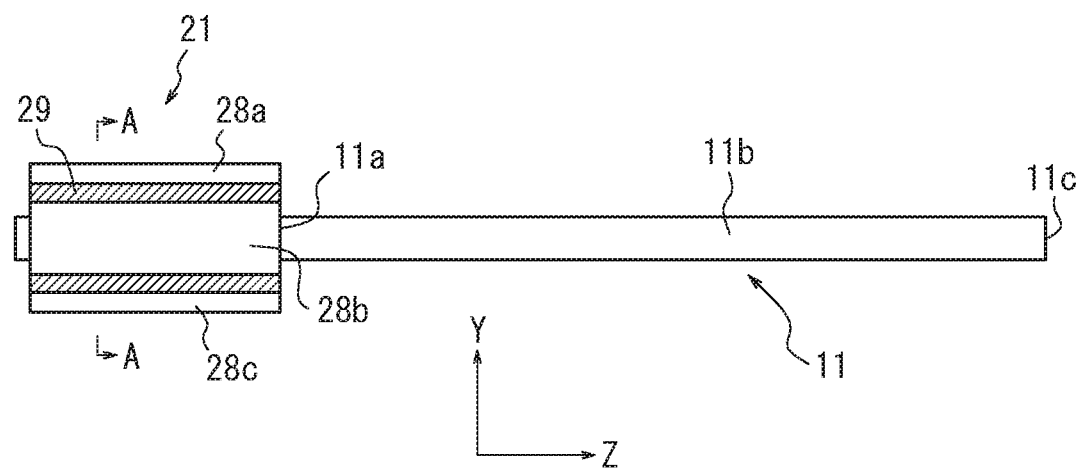
FIG. 4A is a side view.
Figure 4B:
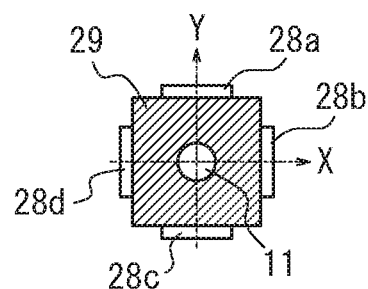
FIG. 4B is a cross-sectional diagram along the A-A line in FIG. 4A, illustrating the driver and the oscillating portion of the optical fiber for illumination in FIG. 3.

FIG. 4A illustrates the vibration driving mechanism of the actuator 21 of the optical scanning endoscope apparatus 10 and illustrates the oscillating part 11b of the light transmission fiber 11. FIG. 4B is a cross-sectional diagram along the A-A line in FIG. 4A. The light transmission fiber 11 passes through the center of the fiber holding member 29, which is shaped as a quadratic prism, and is fixed and held by the fiber holding member 29. The four sides of the fiber holding member 29 respectively face the ±Y direction and the ±X direction. A pair of piezoelectric elements 28a and 28c for driving in the Y direction are fixed onto the sides of the fiber holding member 29 in the ±Y direction, and a pair of piezoelectric elements 28b and 28d for driving in the X direction are fixed onto the sides in the ±X direction.

The wiring cable 13 from the actuator driver 38 of the control device body 30 is connected to the piezoelectric elements 28a to 28d, which are driven by application of voltage by the actuator driver 38.

Voltage of equivalent magnitude and opposite sign is always applied across the piezoelectric elements 28b and 28d in the X direction. Similarly, voltage of equivalent magnitude and opposite sign is always applied across the piezoelectric elements 28a and 28c in the Y direction. One of the piezoelectric elements 28b and 28d disposed opposite each other with the fiber holding member 29 therebetween expands and the other contracts, thereby causing the fiber holding member 29 to flex. Repeating this operation produces vibration in the X direction. The same is true for vibration in the Y direction as well.

The actuator driver 38 can perform vibration driving of the piezoelectric elements 28b and 28d for driving in the X direction and the piezoelectric elements 28a and 28c for driving in the Y direction by applying vibration voltage of the same frequency or vibration voltage of different frequencies thereto. Upon vibration driving of the piezoelectric elements 28a and 28c for driving in the Y direction and the piezoelectric elements 28b and 28d for driving in the X direction, the oscillating part 11b of the light transmission fiber 11 illustrated in FIGS. 3, 4A, and 4B vibrates, and the tip 11c is deflected, so that the laser illumination light emitted from the tip 11c sequentially scans the surface of the object 100 along a predetermined scan path.

Figure 5:
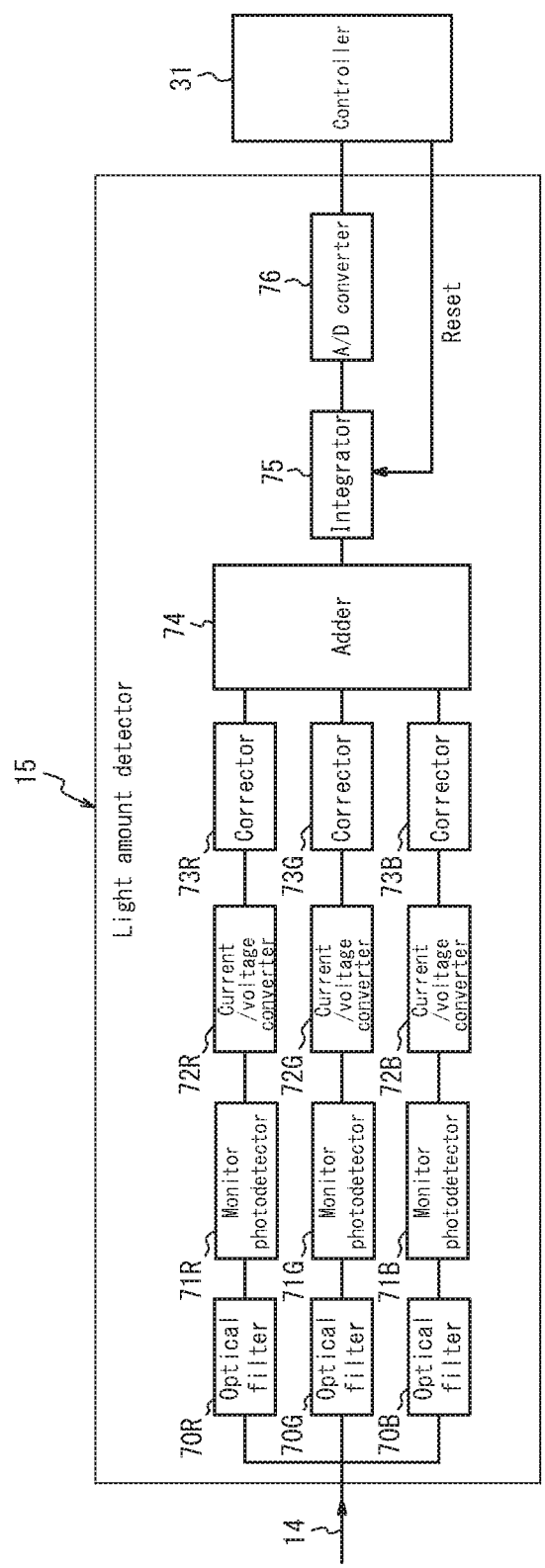
FIG. 5 is a block diagram schematically illustrating the structure of the light amount detector in FIG. 1.

Next, with reference to FIG. 5 and FIGS. 6A to 6D, the light amount detector 15 is described in further detail. FIG. 5 schematically illustrates the structure of the light amount detector 15. FIGS. 6A to 6D illustrate operations by the light amount detector 15 and the controller 31. The light amount detector 15 includes optical filters 70R, 70G, and 70B, monitor photodetectors 71R, 71G, and 71B, current/voltage converters 72R, 72G, and 72B, correctors 73R, 73G, and 73B, an adder 74, an integrator 75, and an analog/digital (A/D) converter 76.

As illustrated in FIG. 6A, the optical filters 70R, 70G, and 70B divide up, by color, the R, G, and B illumination light that is sequentially input from the monitor fiber 14 at each light emission cycle $T_E$ of the light source 33 and output the divided R, G, and B illumination light to the monitor photodetectors 71R, 71G, and 71B provided respectively for the colors R, G, and B.

The monitor photodetectors 71R, 71G, and 71B each detect illumination light from the respective optical filters 70R, 70G, and 70B and output the detection result (current signal) to the current/voltage converters 72R, 72G, and 72B provided respectively for the colors R, G, and B.

The current/voltage converters 72R, 72G, and 72B convert the detection results (current signals) from the monitor photodetectors 71R, 71G, and 71B to respective voltage signals and output the voltage signals to the correctors 73R, 73G, and 73B provided respectively for the colors R, G, and B.

The correctors 73R, 73G, and 73B correct the respective detected signals (voltage signals) of R, G, and B illumination light obtained from the monitor photodetectors 71R, 71G, and 71B via the current/voltage converters 72R, 72G, and 72B in accordance with each wavelength (color) of illumination light and output the results to the adder 74.

In general, the light reception sensitivity of photodetectors such as the monitor photodetectors 71R, 71G, and 71B is dependent on wavelength. Taking this into account, in the correctors 73R, 73G, and 73B, the detected signals (voltage signals) of R, G, and B light obtained from the monitor photodetectors 71R, 71G, and 71B via the current/voltage converters 72R, 72G, and 72B are corrected color by color so that the same voltage signal is obtained for input of the same light amount to the monitor photodetectors 71R, 71G, and 71B.

For example, when the monitor photodetectors 71R and 71B corresponding to R and B respectively output a 200 µA current signal based on 1 mW of R and B input light, and the monitor photodetector 71G corresponding to G outputs a 100 µA current signal based on 1 mW of G input light, then the light reception sensitivities of the monitor photodetectors 71R, 71G, and 71B corresponding to R, G, and B are in a ratio of 2:1:2. In this case, the correctors 73R, 73G, and 73B corresponding to R, G, and B multiply the voltage signals input from the monitor photodetectors 71R, 71G, and 71B via the current/voltage converters 72R, 72G, and 72B respectively by factors of 1, 2, and 1 (i.e. only the corrector 73G corresponding to G doubles the input voltage signal), thus yielding the same voltage signals for the same input light amount.

By providing the correctors 73R, 73G, and 73B, the light amount of illumination light from the light source 33 can be detected more accurately.

The detected signals of light of each color (voltage signals) corrected by the correctors 73R, 73G, and 73B respectively corresponding to R, G, and B are summed by the adder 74, and the result of summation is output to the integrator 75.

The integrator 75 is notified of a reset timing by the controller 31 at predetermined reset intervals $T_R$ (for example, 0.001 seconds). As illustrated in FIG. 6B, upon reaching a reset timing, the integrator 75 starts to integrate the light detection signal input from the correctors 73R, 73B, and 73G via the adder 74, and upon reaching the next reset timing, outputs the result of integration during the immediately prior reset interval $T_R$ to the A/D converter 76 as the light amount of illumination light from the light source 33.

The A/D converter 76 converts the integration result from the integrator 75 to digital data by A/D conversion and notifies the controller 31 of the digital data as the light amount of illumination light from the light source 33.

The controller 31 calculates the integral value I of the light amount of illumination light, from the light source 33, detected during the immediately prior predetermined integration period $T_A$ (for example, 0.25 seconds) by the light amount detector 15 (also referred to below simply as the "integral value I of the light amount"). In other words, as illustrated in FIG. 6C, in each reset interval $T_R$, the reference point of the start of integration shifts by the reset interval $T_R$ (moving integration). The predetermined integration period $T_A$ is set to be longer than the reset interval $T_R$ ($T_A > T_R$). FIG. 6D illustrates the integral value I calculated by the controller 31.

In this embodiment, the controller 31 stores, in advance, a predetermined control threshold $I_T$ of the integral value I of the light amount detected by the light amount detector 15 during the predetermined integration period $T_A$. This predetermined control threshold $I_T$ is set to a lower value than a predetermined allowable limit $I_L$ that the integral value I of the light amount is not supposed to exceed. In this embodiment, the controller 31 compares the integral value I of the light amount with the control threshold $I_T$ at each reset interval $T_R$ and controls the output of the light source 33 based on the result of comparison.

FIGS. 7A to 7C illustrate an example of operations by the controller 31. The integral value I of the light amount calculated in each reset interval $T_R$ in this example is equal to or less than the control threshold $I_T$. In this example, the controller 31 compares the integral value I of the light amount detected by the light amount detector 15 with the control threshold $I_T$ at each reset interval $T_R$ and does not perform special control when, as a result, the integral value I of the light amount is equal to or less than the control threshold $I_T$.

FIGS. 8A to 8C illustrate another example of operations by the controller 31. The integral value I of the light amount detected by the light amount detector 15 in this example exceeds the control threshold $I_T$ at a certain reset timing. In this example, when judging that the integral value I of the light amount exceeds the control threshold $I_T$ as a result of comparing the integral value I of the light amount with the control threshold $I_T$ at each reset interval $T_R$, the controller 31 controls output of the light source 33. Here, the controller 31 preferably controls output of the light source 33 so that the integral value I of the light amount does not exceed the allowable limit $I_L$.

In greater detail, in this example, the controller 31 compares the integral value I of the light amount with the control threshold $I_T$ and lowers the light amount of the light source 33 when the integral value I of the light amount exceeds the control threshold $I_T$. In this case, for example even after initially lowering the light amount of the light source 33, at each reset interval $T_R$ the controller 31 preferably continues to set the light amount of the light source 33 to a value lower than the control threshold $I_T$ until the integral value I of the light amount becomes equal to or less than the control threshold $I_T$.

The light amount of the light source 33 is, for example, preferably lowered to a light amount lower than the average light amount of illumination light from the light source 33 during the immediately prior predetermined integration period $T_A$. Even after initially lowering the light amount of the light source 33, at each reset interval $T_R$ the controller 31 preferably continues to set the light amount of the light source 33 to a light amount lower than the average light amount of illumination light from the light source 33 during the immediately prior predetermined integration period $T_A$ until the integral value I of the light amount becomes equal to or less than the control threshold $I_T$.

According to this embodiment, the light amount of illumination light emitted in a certain period can be controlled.

Furthermore, according to this embodiment, the light amount of illumination light from the light source 33 is calculated using the monitor photodetectors 71R, 71G, and 71B, thus allowing the light amount of illumination light from the light source 33 to be calculated accurately.

One method of calculating the light amount of illumination light from the light source 33 is, for example, to configure the light source 33 with a laser diode and use the input current of the laser diode. In general, however, the relationship between the input current and the output light amount in a laser diode changes over time, and the degree of change over time also varies depending on the color of light. Hence, the light amount of illumination light from the light source 33 cannot be calculated very accurately.

This disclosure is not limited to the above-described embodiments, and a variety of modifications may be made. For example, the controller 31 may suspend output of the light source 33 when the integral value I of the light amount detected by the light amount detector 15 during the immediately prior predetermined integration period $T_A$ exceeds the control threshold $I_T$.

The light amount detector 15 may be formed integrally with the light source 33 as a photodiode (PD). In other words, in this case, the light amount detector 15 is disposed on the upstream side of the combiner 34.

In the example illustrated in FIG. 5, by providing the light amount detector 15 with the optical filters 70R, 70G, and 70B that divide light into R, G, and B light, correction can be made taking into consideration the light reception sensitivity of each color in the correctors 73R, 73G, and 73B even when light of a plurality of colors is input simultaneously, or when the light source 33 is a white light source. Hence, the light amount of illumination light from the light source 33 can be calculated accurately.

In the case of the R, G, and B illumination light being sequentially input into the light amount detector 15, the light amount detector 15 may, instead of including optical filters and an adder, be configured to include one each of a monitor photodetector, a current/voltage converter, a corrector, an integrator, and an A/D converter, and at the timing at which the R, G, and B light is sequentially input, the processing by the corrector may be switched in accordance with the color of light.

A level corrector (not illustrated) may also be provided between the correctors 73R, 73G, and 73B and the adder 74, and level correction may be performed on the signal in accordance with the irradiation distance to the object, irradiation position, and the like.

Figure 9A:
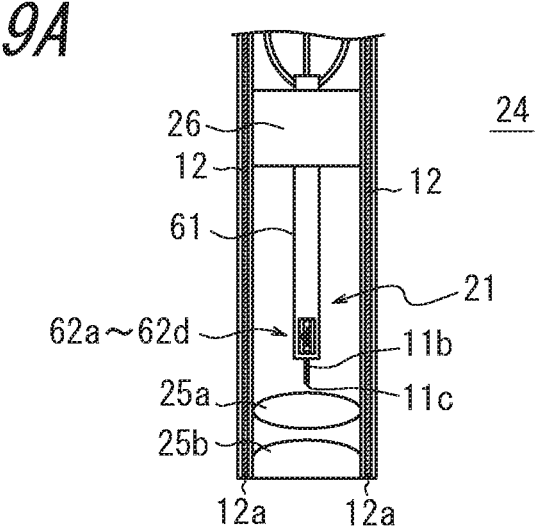
FIGS. 9A to 9C illustrate modifications to the driver in FIGS. 4A and 4B, where
Figure 9B:
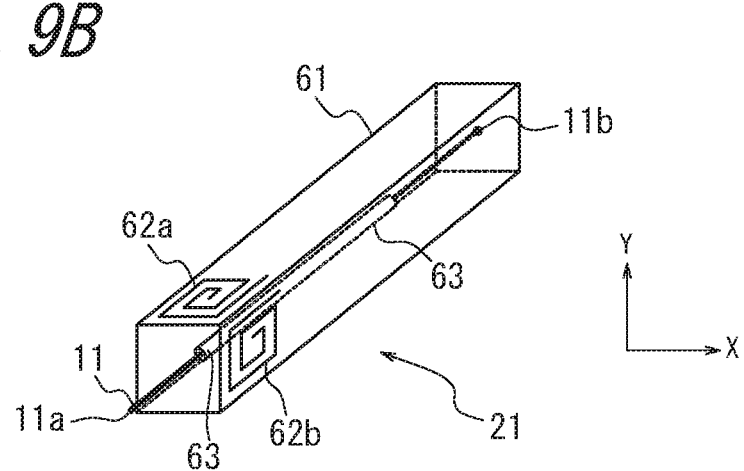
Figure 9C:
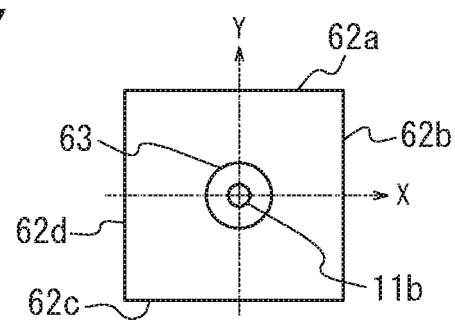

The actuator 21 of the light transmission fiber 11 is not limited to use of piezoelectric elements. For example, a permanent magnet fixed to the light transmission fiber 11 and coils for generation of a deflecting magnetic field (magnet coils) that drive the permanent magnet may be used instead. The following describes a modification to the actuator 21 with reference to FIGS. 9A to 9C. FIG. 9A is a cross-sectional diagram of the tip 24 of the scope 20, FIG. 9B is an enlarged perspective view of the actuator 21 in FIG. 9A, and FIG. 9C is a cross-sectional view along a plane perpendicular to the axis of the light transmission fiber 11, illustrating a portion including the coils 62a to 62d for generation of a deflecting magnetic field and the permanent magnet 63 in FIG. 9B.

At a portion of the oscillating part 11b of the light transmission fiber 11, the permanent magnet 63, which is magnetized in the axial direction of the light transmission fiber 11 and includes a through-hole, is joined to the light transmission fiber 11 by the light transmission fiber 11 being passed through the through-hole. A square tube 61, one end of which is fixed to the attachment ring 26, is provided so as to surround the oscillating part 11b, and flat coils 62a to 62d for generation of a deflecting magnetic field are provided on the sides of the square tube 61 at a portion thereof opposing one pole of the permanent magnet 63.

The pair of coils 62a and 62c for generation of a deflecting magnetic field in the Y direction and the pair of coils 62b and 62d for generation of a deflecting magnetic field in the X direction are each disposed on opposing sides of the square tube 61, and a line connecting the center of the coil 62a for generation of a deflecting magnetic field with the center of the coil 62c for generation of a deflecting magnetic field is orthogonal to a line connecting the center of the coil 62b for generation of a deflecting magnetic field with the center of the coil 62d for generation of a deflecting magnetic field near the central axis of the square tube 61 when the light transmission fiber 11 is disposed therein at rest. These coils are connected to the actuator driver 38 of the control device body 30 via the wiring cable 13 and are driven by driving current from the actuator driver 38.

Furthermore, the scanner is not limited to oscillating the tip of an optical fiber. For example, an optical scanning element such as a MEMS mirror may be disposed along the optical path from the light source 33 to the object.

REFERENCE SIGNS LIST

10 Optical scanning endoscope apparatus
11 Light transmission fiber (scanner)
11a Fixed end
11b Oscillating part
11c Tip
12 Light-receiving fiber
13 Wiring cable
14 Monitor fiber
15 Light amount detector
20 Scope
21 Actuator (scanner)
22 Operation part
23 Insertion part
24 Tip
25a, 25b Projection lens
26 Attachment ring
28a to 28d Piezoelectric element
29 Fiber holding member
30 Control device body
31 Controller
32 Light emission controller
33 Light source
33R, 33G, 33B Laser
34 Combiner
35 Photodetector for reception light
36 ADC
37 Signal processor
38 Actuator driver
40 Display
61 Square tube
62a to 62d Coil for generation of a deflecting magnetic field
63 Permanent magnet
70R, 70G, 70B Optical filter
71R, 71G, 71B Monitor photodetector
72R, 72G, 72B Current/voltage converter
73R, 73G, 73B Corrector
74 Adder
75 Integrator
76 A/D converter
100 Object

The invention claimed is:

1. An optical scanning endoscope apparatus comprising:
 a scanner configured to scan an object with illumination light from a light source;
 a light amount detector configured to detect, at predetermined time intervals, a light amount of the illumination light from the light source; and
 a controller comprising hardware, the controller being configured to:
  compare, whenever the light amount is detected by the light amount detector, an integral value of the light amount during a predetermined period immediately prior to the detecting, with a predetermined threshold, and
  control output of the light source when the integral value of the light amount exceeds the predetermined threshold, the predetermined period being set to be longer than the predetermined time interval.

2. The optical scanning endoscope apparatus of claim 1, wherein the controller is further configured to suspend the output of the light source when the integral value of the light amount exceeds the predetermined threshold.

3. The optical scanning endoscope apparatus of claim 2, wherein when the integral value of the light amount exceeds the predetermined threshold, the controller is configured to control the output of the light source so that the integral value of the light amount does not exceed a predetermined allowable limit that is higher than the predetermined threshold.

4. The optical scanning endoscope apparatus of claim 2, wherein the light amount detector comprises:
 a monitor photodetector configured to detect the illumination light from the light source;
 a corrector configured to correct a light detection signal from the monitor photodetector in accordance with wavelength of the illumination light; and
 an integrator configured to calculate the light amount based on the light detection signal corrected by the corrector.

5. The optical scanning endoscope apparatus of claim 2, wherein a reference point of a start of integration of the integral value of the light amount shifts by the predetermined time interval.

6. The optical scanning endoscope apparatus of claim 1, wherein the controller is further configured to lower the light amount of the illumination light from the light source when the integral value of the light amount to a light amount lower than an average light amount exceeds the predetermined threshold of the illumination light from the light source during the predetermined period immediately prior to the detection of the light amount of the illumination light from the light source.

7. The optical scanning endoscope apparatus of claim 6, wherein when the integral value of the light amount exceeds the predetermined threshold, the controller is configured to control the output of the light source so that the integral value of the light amount does not exceed a predetermined allowable limit that is higher than the predetermined threshold.

8. The optical scanning endoscope apparatus of claim 6, wherein the light amount detector comprises:
 a monitor photodetector configured to detect the illumination light from the light source;
 a corrector configured to correct a light detection signal from the monitor photodetector in accordance with wavelength of the illumination light; and an integrator configured to calculate the light amount based on the light detection signal corrected by the corrector.

9. The optical scanning endoscope apparatus of claim 6, wherein a reference point of a start of integration of the integral value of the light amount shifts by the predetermined time interval.

10. The optical scanning endoscope apparatus of claim 1, wherein when the integral value of the light amount exceeds the predetermined threshold, the controller is configured to control the output of the light source so that the integral value of the light amount does not exceed a predetermined allowable limit that is higher than the predetermined threshold.

11. The optical scanning endoscope amlaratus of claim 10, wherein a reference point of a start of integration of the integral value of the light amount shifts by the predetermined time interval.

12. The optical scanning endoscope apparatus of claim 1, wherein the light amount detector comprises:
a monitor photodetector configured to detect the illumination light from the light source;
a corrector configured to correct a light detection signal from the monitor photodetector in accordance with wavelength of the illumination light; and
an integrator configured to calculate the light amount based on the light detection signal corrected by the corrector.

13. The optical scanning endoscope apparatus of claim 12, wherein a reference point of a start of integration of the integral value of the light amount shifts by the predetermined time interval.

14. The optical scanning endoscope apparatus of claim 1, wherein a reference point of a start of integration of the integral value of the light amount shifts by the predetermined time interval.

15. A method of controlling an optical scanning endoscope apparatus, the method including:
scanning an object with illumination light from a light source;
detecting, at predetermined time intervals, a light amount of the illumination light from the light source; and
comparing, whenever the light amount is detected by the light amount detector, an integral value of the light amount during a predetermined period immediately prior to the detecting, with a predetermined threshold, and controlling output of the light source when the integral value of the light amount exceeds the predetermined threshold, the predetermined period being set to be longer than the predetermined time interval.

* * * * *